United States Patent [19]

Sherman et al.

[11] Patent Number: 5,596,995

[45] Date of Patent: Jan. 28, 1997

[54] BIOMEDICAL DEVICE HAVING A TEMPERATURE SENSING SYSTEM

[75] Inventors: Marshall L. Sherman, Cardiff; Thomas M. Castellano; José J. Moya, both of Temecula, all of Calif.

[73] Assignee: Heart Rhythm Technologies, Inc., Temecula, Calif.

[21] Appl. No.: 432,837

[22] Filed: May 2, 1995

[51] Int. Cl.⁶ .................................................. A61B 5/00
[52] U.S. Cl. ............................................................. 128/736
[58] Field of Search ................................... 128/736, 670; 606/31; 607/62, 99, 122

[56] References Cited

U.S. PATENT DOCUMENTS

| | | | |
|---|---|---|---|
| 3,935,744 | 2/1976 | Beckman | 128/736 |
| 5,383,923 | 1/1995 | Webster, Jr. | 607/125 |
| 5,405,346 | 4/1995 | Grundy et al. | 606/41 |
| 5,425,375 | 6/1995 | Chin et al. | 128/736 |
| 5,447,529 | 9/1995 | Marchlinski et al. | 607/99 |

*Primary Examiner*—Max Hindenburg
*Attorney, Agent, or Firm*—Fulwider Patton Lee & Utecht, LLP

[57] ABSTRACT

A system for monitoring temperature comprising a first thermocouple temperature sensor mounted to a catheter, the catheter also having a connector with a plurality of connecting devices for making the thermocouple signals available to external equipment. The connecting devices are formed of a material dissimilar to at least one of the thermocouple leads such that a second thermocouple is created at the connection point. The second thermocouple produces a second temperature signal that combines with the signal from the first thermocouple. A reference temperature sensor is mounted at the connector to sense the temperature at the connector and provide a reference temperature signal for use by a processor in correcting the combined temperature signal to derive the first thermocouple signal received from the connector.

14 Claims, 2 Drawing Sheets

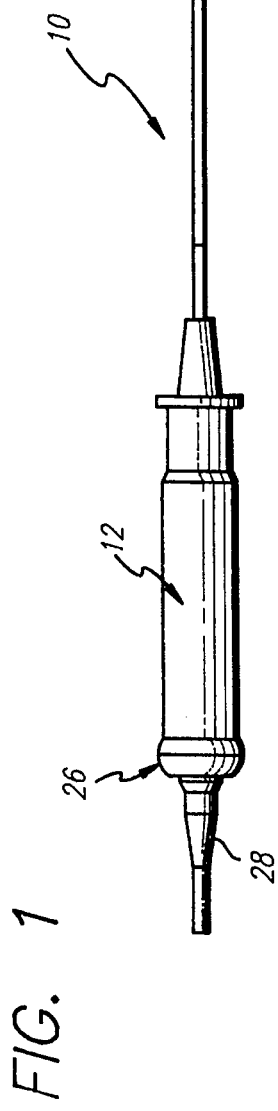
FIG. 1
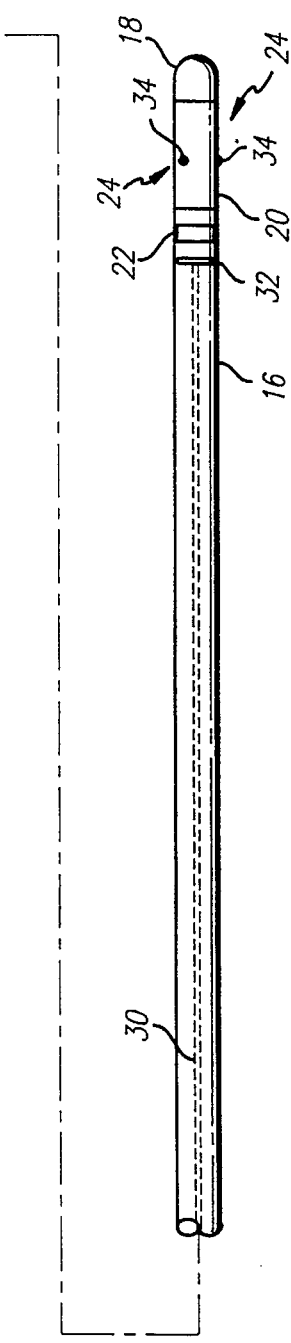
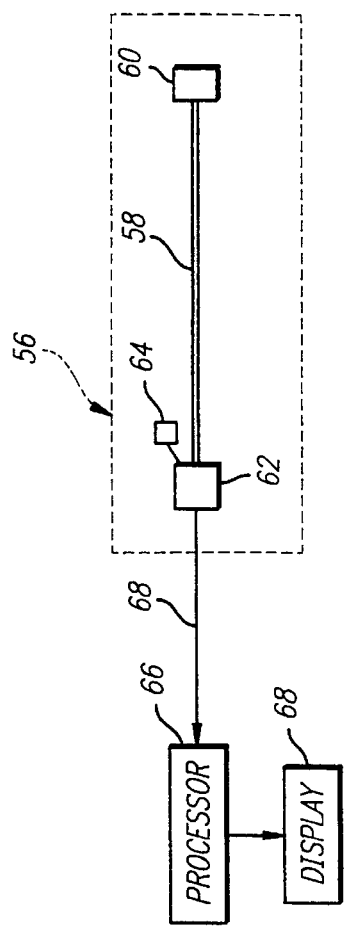
FIG. 4

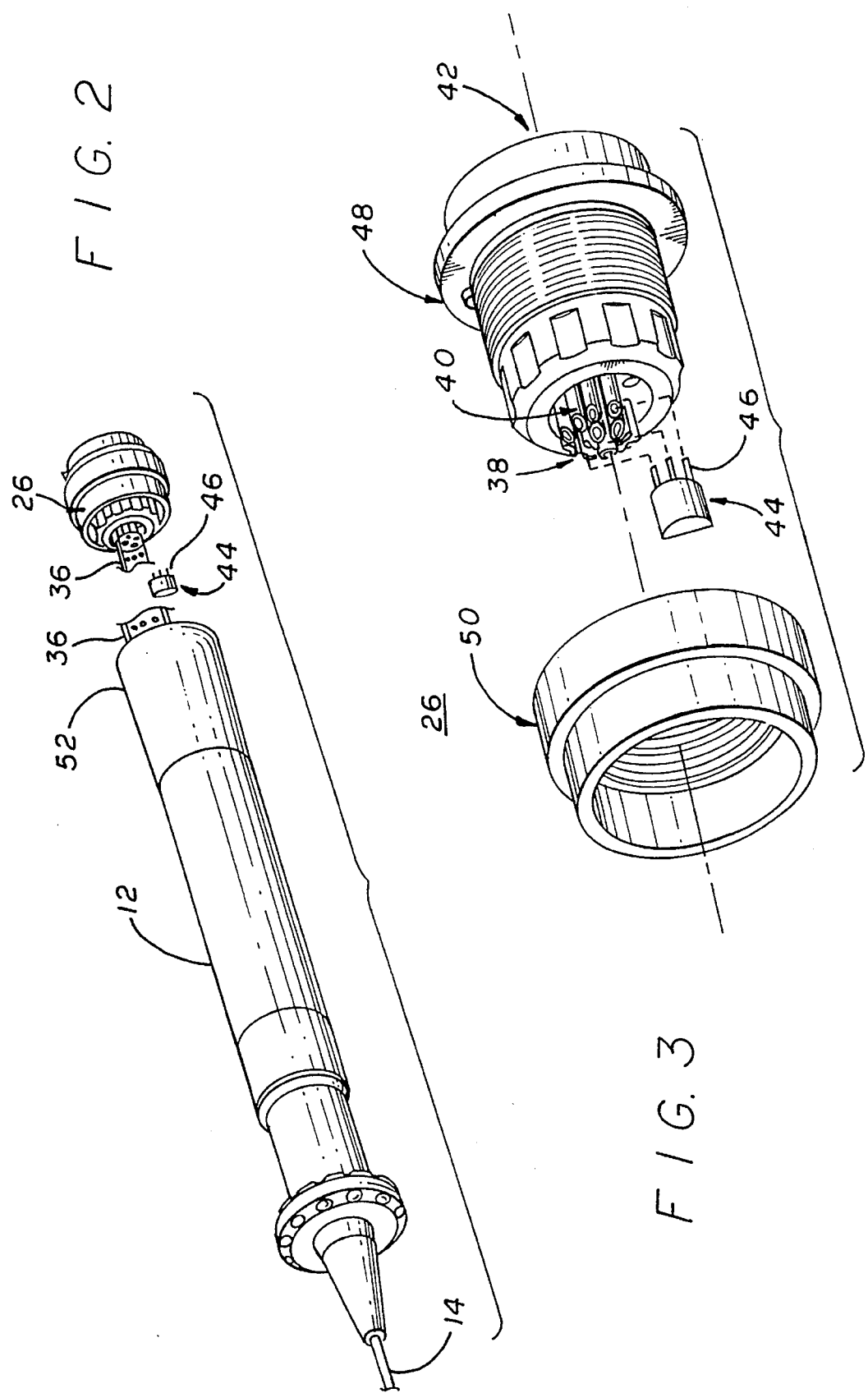

BIOMEDICAL DEVICE HAVING A TEMPERATURE SENSING SYSTEM

BACKGROUND

The invention is generally related to biomedical devices for sensing physiological parameters and, more particularly, to catheters having temperature sensing devices.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation is a procedure often successful in terminating cardiac arrhythmia. This procedure involves applying sufficient energy to the interfering tissue to ablate that tissue thus removing the irregular signal pathway. However, before an ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology ("EP") catheter having mapping electrodes mounted on its distal extremity. The catheter is maneuvered to place those electrodes in contact with or in close proximity to the endocardium of the patient's heart. By monitoring the electrical signals at the endocardium, aberrant conductive tissue sites responsible for the arrhythmia can be pinpointed.

Once the origination point for the arrhythmia is located in the tissue, the physician may use an ablation procedure to destroy the tissue causing the arrhythmia an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

The distal end of an EP catheter may include the mapping electrodes as well as an ablation device mounted near the tip for performing the ablation procedure. One type of ablation device includes an ablation electrode that emits radio frequency ("RF") energy to heat the target tissue to a temperature high enough to cause ablation of that tissue. Other types of ablation devices may be used and in the following disclosure, an ultrasonic device is disclosed.

As the ablation procedure progresses, heat is generated and the surrounding blood is exposed to this heat. At approximately 90°–100° C., charring and boiling of the blood take place. Charring is particularly troublesome at the surface of the ablation device because emboli may form on the surface of the device to an extent that the catheter must be removed and cleaned before the procedure can continue. Furthermore, in RF ablation procedures, charring can cause a substantial increase in the impedance and a corresponding decrease in the power delivery to the tissue. Too great a rise in impedance can result in sparking and thrombus formation within the heart, both of which are undesirable.

Because part of the ablation transducer is in contact with the blood in the heart, blood boiling, emboli development, and clotting can result if the surface temperature of the transducer exceeds 90°–100° C. If this occurs, the ablation procedure must be stopped regardless of whether the entire ablation procedure has been completed. The catheter must then be removed from the patient, the attached necrotic tissue removed, and the catheter reinserted into the patient. Such cleaning processes require extra time and unduly prolong the ablation procedure. To avoid such undesirable circumstances, a temperature sensor may be incorporated at the distal end of the catheter to monitor and maintain a selected temperature during ablation. The ablation process can then be controlled so that the temperature is not allowed to increase above a predetermined level.

Temperature sensors have been incorporated in catheters for some time. One of these temperature sensors comprises a thermocouple having elongated sensing joined together at their distal ends to form the thermocouple and their proximal ends connected to a connector mounted in the catheter. External equipment may be connected to the connector of the catheter to receive the temperature signals of the thermocouple for processing to determine the temperature sensed. The thermocouple is typically disposed at the distal end of the catheter.

Thermocouples use two leads formed of dissimilar materials, for example one lead formed of constantan and the other lead formed of copper, that are joined at one end to form a thermocouple junction. The thermocouple junction produces a voltage representative of the temperature at the junction and that voltage varies as the junction is exposed to temperature changes. The proximal ends of the leads of dissimilar materials are commonly directed within the catheter to the connector and are connected to connecting devices, such as pins, of that connector. The connector is typically formed with a plurality of metallic connecting devices to which the thermocouple leads and other leads are soldered. If those connecting devices are composed of a material dissimilar to a material of the thermocouple leads, for example copper, then when the constantan thermocouple lead is connected to the copper connecting device, a second thermocouple junction will be formed at that connection point. This second thermocouple junction will also produce a voltage dependent on the temperature of that particular junction and because it is part of the electrical circuit of the distal end thermocouple, this additional voltage will combine with the distal end thermocouple signal resulting in reduced accuracy of the temperature indication of the distal tip of the catheter.

While custom connectors and interconnection cables may be built having certain pins formed of constantan and some of copper, for example, so that thermocouples at the connector are not formed, such devices can be relatively expensive. It would be desirable to be able to use standard, less expensive devices.

Hence, those skilled in the art have recognized the need for a temperature sensing system that compensates for thermocouple effects produced at the connection points in the catheter handle to produce a more accurate temperature indication. A need has also been recognized for such a system that does not significantly increase the expense of the catheter yet provides increased accuracy. The present invention fulfills these needs and others.

SUMMARY OF THE INVENTION

The present invention is directed to a temperature sensing system for a biomedical device that maintains the accuracy of the temperature signal from a temperature sensor mounted on the biomedical device.

Briefly and in general terms, the biomedical device includes a temperature sensor having temperature sensor leads mounted in a housing. The housing also mounts therein a connector including a plurality of connecting devices having first and second ends. The sensor leads of the temperature sensor are connected to the respective first ends of the connecting devices to receive a first temperature signal from the temperature sensor and conduct that first temperature signal to the second ends of the connecting devices. The connection between the ends of the sensor leads and the first ends of the connecting devices causes a second temperature signal that is conducted to the second ends of the connecting devices such that a combined temperature signal comprising both the first and second temperature signals is made available to external equipment adapted for connection to such second ends of the connecting devices. The temperature sensing system further includes a reference temperature sensor mounted at the connector to sense the temperature at the connector and provide a temperature reference signal usable to compensate for the effect on the first temperature sensor signals that the second temperature signal imposes.

In a more particular aspect of the invention, the first temperature sensor leads comprise two leads of dissimilar materials joined together at their distal ends to define a first thermocouple that provides the first temperature signal. In a further aspect, the connecting devices are formed of a material dissimilar to at least one of the first temperature sensor leads wherein the proximal ends of the two leads are connected at their proximal ends to the respective first ends of the connecting devices to cream a second thermocouple that causes the second temperature signal.

In a more detailed aspect of the invention, the reference temperature sensor comprises a non-thermocouple device, the output of which comprises the temperature reference signal.

In a further aspect of the invention, the non-thermocouple temperature sensor comprises a semi-conductor and in another aspect, the non-thermocouple temperature sensor comprises a thermistor.

In yet a further aspect, the reference temperature sensor is mounted directly to the connector.

In a more particular aspect of the invention, the biomedical device comprises a catheter with the first temperature sensor disposed at the distal end of the catheter. The connector is located at the proximal end of the catheter with the reference temperature sensor mounted directly to the connector to provide the reference signal.

In a further aspect, the temperature sensing system further includes a processor coupled to the connector. The processor receives the temperature signal of the first temperature sensor that has been combined with the thermocouple signal created by connecting its lead to the connector, receives the reference signal from the reference temperature sensor, and adjusts the combined first temperature signal in accordance with the reference signal to provide a more accurate indication of temperature at the first temperature sensor.

Other features and advantages of the invention will become apparent from the following detailed description taken in conjunction with the accompanying drawings, which illustrate by way of example, the features and advantages of the invention.

BRIEF DESCRIPTION OF THE DRAWINGS

FIG. 1 is a side view of a biomedical device, shown as a catheter, including a first temperature sensor mounted at the distal end for sensing temperature, and a handle at the proximal end containing a connector and a reference temperature sensor in accordance with principles of the invention;

FIG. 2 is an exploded perspective view of part of the catheter handle and connector of the catheter shown in FIG. 1;

FIG. 3 is an exploded perspective view of the connector shown in FIG. 2; and

FIG. 4 is a block diagram of a temperature sensing system having a first temperature sensor, a reference temperature sensor, and a processor that adjusts the thermocouple signals in accordance with the reference sensor signals.

DETAILED DESCRIPTION OF THE PREFERRED EMBODIMENTS

In the following description, like reference numerals are used to designate like or corresponding elements among the several figures of the drawings. Referring now to the drawings and particularly to FIG. 1 there is shown a biomedical device, or more particularly, a catheter 10 usable for electrophysiological procedures and embodying features of the invention.

The catheter 10 includes, in this case, a manipulation handle 12 mounted to the proximal end of an elongated catheter tube or body member 14 having a distal end 16 with an electrode 18 mounted at the distal tip, a cylindrical piezoelectric transducer 20 mounted proximal to the tip electrode, and an axially spaced apart band electrode 22 mounted proximal to the piezoelectric transducer. A number of temperature sensors 24, are mounted on the piezoelectric transducer 20 for sensing temperature adjacent the sensors. The manipulation handle houses an electrical connector 26 and in this case the connector comprises a receptacle device (female) for accepting a complementary male connector of a cable 28 for conducting signals between the catheter and external equipment. For purposes of clarity, the receptacle of this embodiment is referred to herein as a connector. The external equipment may include a processing system for processing signals received from the catheter to provide the clinician with sensed electrophysiological information.

In this embodiment, a body member deflection control device is disposed within the catheter body member 14 and has its distal end located at the distal end 16 of the body member. The deflection control device includes a deflection control line 30 used to impart deflection forces to the body member causing the body member to deflect in a controlled manner for directing the catheter to endocardial sites in the heart of the patient. The distal tip of the deflection line 30 is fixed to an anchor plate 32 in the distal end 16 of the catheter body member 14.

The electrodes 18 and 22 and piezoelectric transducer 20 may be individually or simultaneously actuated to perform various electrophysiological procedures. For instance, the distal tip electrode 18 may be an EP mapping-type electrode such that when the distal end 16 of the catheter 10 is introduced into the intracardial volume of the heart, the electrode receives electrical signals from adjacent endocardial tissue. By analyzing those electrical signals, aberrant conductive tissues that cause cardiac arrhythmia can be located. The band electrode 22, proximal to the piezoelectric transducer 20, may also be used either individually or simultaneously with the tip electrode to perform EP mapping procedures.

The cylindrical piezoelectric transducer 20, in this case, is a side-fire ablation-type transducer that directs ultrasonic acoustic energy in a radial outward direction. When the site of the aberrant conductive tissue has been located, the transducer may be positioned adjacent that site and activated to transmit ultrasonic energy to that aberrant tissue. The ultrasonic energy ablates the target tissue. A particular catheter having an ultrasonic ablation transducer is disclosed in a co-pending application entitled "Catheter Having Ultrasonic Device", inventor Thomas Castellano, and filed the same day as the present application and is herein incorporated by reference.

Although two sensing electrodes 18 and 22 and one ablation transducer 20 are shown, more or fewer of each of these devices may be used depending on the application. Additionally, the types of devices mentioned for sensing and ablation are only for purposes of illustration.

As discussed above, the ablation procedure may expose blood to high temperature unless the temperatures is monitored and the ablation energy controlled. To avoid excessive temperature, the temperature sensors 24 are used to monitor the temperature surrounding the ablation transducer so that hospital clinicians can regulate the ablation procedure accordingly.

Referring to FIG. 1, three temperature sensors 24 (only two shown) are mounted at the surface of the cylindrical piezoelectric transducer 20 to sense temperature at those points. The three temperature sensors 24 are disposed in an orthogonal plane relative to the central axis of the transducer 20. For purpose of illustration, three sensors are provided, however, more or fewer sensors may be mounted in the transducer. Having a greater number of temperature sensors in the transducer may be more desirable in certain applications.

More particularly, each of the temperature sensors 24 is in the form of a point sensor mounted within small sensor holes (not shown) formed through the wall of the transducer 20. It is desirable that the temperature sensors be as small as possible so that when the devices are mounted in the sensor bore holes of the piezoelectric transducer 20, the transducer's ultrasonic performance is minimally affected.

In particular, point thermocouples 34 are preferably used as the temperature sensors 24 due to their small size and rapid temperature sensing characteristics. Each thermocouple includes a pair of elongated, insulated flexible electrical temperature sensor leads (not shown) including respective electrically conductive wires formed of dissimilar materials. The distal portion of each wire is stripped of its insulation and is joined with the stripped distal portion of the other lead to form the thermocouple. In one embodiment, one wire is formed of copper and the other wire is formed of constantan. Alternatively, the thermocouple may be constructed of other dissimilar metallic materials. The electrical sensor leads may be forty-four gauge (AWG) bifilar wire available from Hudson International of Trenton, Ga.

The distal portions of the temperature sensor leads may be joined or bonded together, for instance by conductive solder or welding, to form a thermocouple point junction at the solder joint. The thermocouple 34 creams a voltage in response to the temperature it is exposed to and the temperature sensor leads conduct that voltage as temperature sensing signals responsive to the temperature sensed at the thermocouple 34 to external monitoring equipment that derive a temperature indication of the temperature sensed by the thermocouple.

When the catheter is assembled, the proximal ends of the temperature sensor leads are received through the sensor holes in the transducer 20 from the outside of the transducer such that the thermocouple 34 is positioned substantially at the same level or flush with the outer surface of the transducer. Because the thermocouples are located substantially at the outer surface of the cylindrical transducer, the thermocouples are able to sense the temperature of the ablated tissue, the flowing blood and the surface temperature of the transducer itself very rapidly.

With continued reference to FIG. 1, the body member 14 has an inner lumen (not shown) that extends to the distal end 16 of the catheter and that has disposed therein an electrical ablation conductor (not shown) having a distal end electrically connected to the ablation transducer 20. Also extending within the inner lumen are a plurality of electrical mapping conductors (not shown) that have distal ends electrically connected to the sensing electrodes 18 and 22. The proximal ends of the respective mapping conductors, ablation conductors and temperature sensor leads are directed within the inner lumen of the body member 14 to the proximal end of the manipulation handle for connection to the connector 26 of the handle 12.

Referring now to FIG. 2, the proximal ends of the electrode conductors and temperature sensor leads, collectively indicated at 36, are connected to the connector 26. Mounted in an axial orientation within the connector are a plurality of metallic connecting devices 38, shown as connector sockets to which the conductive leads 36 are connected by soldering, for example. Each lead is inserted into a respective socket and soldered in place. The connector devices may also be connector pins or other suitable devices for attaching the conductive leads 36 thereto. The connecting devices are formed of an electrically conductive material such as gold, copper, or gold plated copper, or other material and each has an inner first end 40, to which the thermocouple leads are connected, and an outer second end 42, to which an external connector of the cable 28 (FIG. 1) can be connected.

Because the connecting devices or sockets 38 are formed of a material that is dissimilar to the leads of the thermocouple, a second thermocouple junction is created at the inner ends 40 of the connecting devices 38 by virtue of their connection together. For example, it has been found that connecting a constantan thermocouple lead to a gold plated connector socket causes a thermocouple junction as does connecting a copper thermocouple lead to a gold connector socket, although to a lesser extent. The thermocouples created by these connector connections produce voltages that combine with the voltage from the distal end thermocouple 34 due to their existing in the same electrical circuit. The combined voltage temperature signal is conducted to the outer ends 42 of the connecting devices where they are made available to external equipment via the connection through the cable 28 (FIG. 1). The second voltage component from the second thermocouple may significantly alter the distal end thermocouple's voltage thus causing a temperature indication that may vary from the actual temperature. In one case, the thermocouples produced by the handle connection with the thermocouple leads caused a five degree variance with the actual temperature sensed at the distal end.

For example, in the clinical setting the distal end 16 of the catheter 10 may experience a temperature of 37 degrees C.

(98.6 degrees F.) while the manipulation handle, located outside the patient, experiences operating room temperature, for instance 20 degrees C. (68 degrees F.). The effect of the thermocouples in the handle connection may alter the temperature indicated by the distal thermocouple to other than 37 degrees C.

To increase the accuracy of the temperature sensing system using the distal end thermocouple 34, a reference temperature sensor 44 is mounted closely adjacent the second thermocouple connection points at the inner end 40 of the connecting devices 38 to provide a reference temperature signal in accordance with the temperature at those connection points. The reference temperature may be used to provide a temperature correction factor to compensate for the component of the second thermocouple voltage whereby the thermocouple signal can be adjusted to remove that second voltage component from the temperature signal.

The reference temperature sensor 44 is preferably a "non-thermocouple" type of sensor and may comprise a semi-conductor or a thermistor. One temperature sensor of this type is made available from National Semiconductor under Part No. LM35CZ. The reference temperature sensor in the embodiment shown is generally in the shape of a half cylinder and is relatively small. The reference temperature sensor includes three conductive leads or pins 46 for providing a reference temperature signal representative of the temperature sensed by the sensor.

With reference to FIG. 3, the connector 26 includes a generally cylindrical connector body 48 and a threaded adapter ring 50 for connecting the body to the manipulation handle 12 (FIG. 2). Three of the inner ends 40 of the connecting devices 38 are connected to the reference temperature sensor 44. Three adjacent inner ends 40 of the connecting devices are used to securely mount the reference sensor directly to the connector. The proximal ends of the conductive pins 46 may be connected to the respective connecting devices, for instance, by electrically conductive solder. The reference temperature signal is conducted from the inner ends 40 to the outer ends 42 of the connecting devices where it is made available to external equipment via the connection through the cable 28 (FIG. 1).

To mount the connector 26 to the manipulation handle 12, the adapter ring 50 is threaded onto the connector body 48. Adhesive is then applied to the outer surface of the adapter ring and the ring is received within the open end 52 of the manipulation handle 12 such that the adhesive securely affixes the connector to the handle. When used in the clinical setting, the cable 28 (FIG. 1) having a male connector plug is plugged into a complementary mating socket at the back end of the connector 26 to make electrical contact with outer ends 42 of the connecting devices 38 to conduct the temperature signals and other signals to external instrumentation and other monitoring equipment.

Referring now to the block diagram of FIG. 4, the temperature sensing system for monitoring the temperature of a biomedical device will be described in more detail. The biomedical device, comprising a catheter in this embodiment, is indicated schematically at 56 and includes the catheter body member 58 housing temperature sensor leads therein that connect the distal end thermocouple 60 with the connector 62 at the proximal end of the body member, the connections between the leads and the connector forming a second thermocouple. The reference temperature sensor, indicated at 64, is connected adjacent the connector. The system includes a temperature signal processor 66 connected to the connector 62 by the cable 68 to process the combined temperature signals from the distal end thermocouple 60 and second thermocouple at the connector 62 and to process temperature reference signals from the reference temperature sensor 64. A display 70 is provided to display the temperature sensed by the distal end thermocouple 60.

In operation, the sensing leads conduct a first temperature signal from the thermocouple 60 at the distal end of the biomedical device 56 to a first end of the connecting devices in the connector 62. The second thermocouple junction created because of the attachment of the sensor leads to the first ends of the connecting devices produces a second temperature signal. Because the first and second thermocouples are in the same electrical circuit, the second temperature signal combines with the first temperature signal providing a combined temperature signal at the second ends of the connecting devices.

The processor 66 receives the combined temperature signal with the first and second temperature signal components and the reference temperature signal from the reference temperature sensor 64 from the second ends of the connecting devices via the cable 68. The combined temperature signal and the reference temperature signal are received by the processor independently of each other. The processor then adjusts the combined temperature signal in accordance with the reference temperature signal to eliminate the second temperature signal component from the combined temperature signal. Adjustment is performed by means well known to those skilled in the art. For example, where a copper/constantan junction is used as the distal end thermocouple and a constantan/copper thermocouple junction is formed at the connector 62, a specific voltage per temperature unit is used; e.g. 42 µV/°C. If the temperature at the connector is 22° C., a voltage of 0.924 mV will be produced by this second thermocouple which will lower the voltage from the first thermocouple. If the distal end is experiencing 85° C., it will produce 3.57 mV. But because the connector thermocouple is in the circuit, the combined temperature signal from the connector will only be 2.646 mV (3.57–0.924). However, the processor will read the reference temperature signal of 22° C., calculate a reference component of 0.924 mV (22° C.×42 µV/°C.) from that temperature and add that reference component to the combined temperature signal of 2.646 mV to result in 3.57 mV. By division, the processor then determines that the correct distal end temperature is 85° C. (3.57 V/42 µV/°C.).

The display 70 receives the corrected signal to display an accurate temperature indication of the temperature at the distal end of the biomedical device, or catheter in this case. With accurate information concerning the temperature at the distal end of the catheter, the clinician can properly control the ablation procedure.

The above-described approach results in the temperature compensation capability being located in the catheter, rather than externally. As a result, specialized connectors and cables leading from the catheter to the external instrumentation are not necessary. Standard cables and connectors may be used thus lowering the connection cost. Where a relatively inexpensive reference temperature sensor is used, such as the one mentioned above, the expense of the temperature compensation system is reduced.

While particular embodiment of the invention have been illustrated and described, various modifications can be made without departing from the spirit and scope of the invention. Accordingly, it is not intended that the invention be limited, except as by the appended claims.

What is claimed is:

1. A biomedical device having a temperature sensing system, comprising:

a connector mounted in the biomedical device and including a plurality of connecting devices having first and second ends, the connecting devices conducting signals between respective first and second ends;

a first temperature sensor providing a first temperature signal mounted to the biomedical device having sensor leads connected to respective first ends of the connecting devices;

wherein the connection of a first temperature sensor lead to a first end of a connecting device creates a second temperature signal that combines with the first temperature signal to form a combined temperature signal, the connecting device conducting the combined temperature signal to its second end; and a reference temperature sensor mounted at the connector to sense the temperature at the connector and to provide a temperature reference signal.

2. The biomedical device of claim 1 wherein the first temperature sensor leads comprise two leads of dissimilar materials joined together at their distal ends to provide a first thermocouple and the proximal ends of the two leads connected at their proximal ends to the respective first ends of the connecting devices of the connector; and wherein the connecting devices are formed of a material dissimilar to at least one of the first temperature sensor leads whereby a second thermocouple is created at the connection of the proximal ends of the leads and the first ends of the respective connecting devices.

3. The biomedical device of claim 1 wherein the reference temperature sensor comprises a non-thermocouple device, the output of which comprises the temperature reference signal.

4. The biomedical device of claim 3 wherein the non-thermocouple device comprises a semi-conductor, the output of which comprises the temperature reference signal.

5. The biomedical device of claim 3 wherein the non-thermocouple device comprises a thermistor, the output of which comprises the temperature reference signal.

6. The biomedical device of claim 1 wherein the biomedical device further comprises:

a catheter; and wherein the first temperature sensor is disposed at a distal end of the catheter and the connector is located at a proximal end of the catheter.

7. The biomedical device of claim 6 wherein the reference temperature sensor is mounted directly to the connecting devices of the connector at the proximal end of the catheter.

8. The biomedical device of claim 1 further comprising:

a processor connected to the second ends of the connector devices that receives the combined temperature signal from the second ends of the connecting devices and adjusts the combined temperature signal in accordance with the reference temperature signal to derive the first temperature signal.

9. A catheter having a temperature sensing system comprising:

an elongated body member;

a connector mounted at a proximal end of the body member and having a plurality of connecting devices having first and second ends;

a first temperature sensor providing a first temperature signal mounted to the biomedical device having sensor leads connected to respective first ends of the connecting devices;

wherein the connection of a first temperature sensor lead to a first end of a connecting device creates a second temperature signal that combines with the first temperature signal to form a combined temperature signal, the connecting device conducting the combined temperature signal to its second end; and a reference temperature sensor mounted at the connector to sense the temperature at the connector and to provide a temperature reference signal.

10. The catheter of claim 9 wherein the reference temperature sensor comprises a non-thermocouple device, the output of which comprises the temperature reference signal.

11. The catheter of claim 10 wherein the non-thermocouple device comprises a semi-conductor, the output of which comprises the temperature reference signal.

12. The catheter of claim 10 wherein the non-thermocouple device comprises a thermistor, the output of which comprises the temperature reference signal.

13. The catheter of claim 9 wherein the reference temperature sensor is mounted directly to the connecting devices of the connector at the proximal end of the catheter.

14. The catheter of claim 9 further comprising:

a processor connected to the connector that receives a first temperature signal from the first temperature sensor, receives a second temperature signal from the reference temperature sensor and adjusts the first temperature signal in accordance with the second temperature signal to derive the first temperature signal.

* * * * *